United States Patent
Hamadeh

(10) Patent No.: US 9,468,412 B2
(45) Date of Patent: Oct. 18, 2016

(54) SYSTEM AND METHOD FOR ACCURACY VERIFICATION FOR IMAGE BASED SURGICAL NAVIGATION

(75) Inventor: Mohamed Ali Hamadeh, Kingston, OH (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 2595 days.

(21) Appl. No.: 11/767,281

(22) Filed: Jun. 22, 2007

(65) Prior Publication Data

US 2008/0319311 A1    Dec. 25, 2008

(51) Int. Cl.

| A61B 5/05 | (2006.01) |
|---|---|
| A61B 6/12 | (2006.01) |
| G06T 7/60 | (2006.01) |
| A61B 5/06 | (2006.01) |

(52) U.S. Cl.
CPC . *A61B 6/12* (2013.01); *G06T 7/60* (2013.01); *A61B 5/06* (2013.01)

(58) Field of Classification Search
USPC ........ 600/429, 424, 417, 425, 426; 378/207; 250/370
See application file for complete search history.

(56) References Cited

U.S. PATENT DOCUMENTS

| 5,389,101 | A  | * | 2/1995 | Heilbrun et al. | ............. 606/130 |
|---|---|---|---|---|---|
| 5,603,318 | A  | * | 2/1997 | Heilbrun et al. | ............. 600/426 |
| 6,129,668 | A  | * | 10/2000 | Haynor et al. | ................ 600/424 |
| 6,470,207 | B1 | * | 10/2002 | Simon et al. | ................ 600/426 |
| 6,484,049 | B1 | * | 11/2002 | Seeley et al. | ................ 600/426 |
| 6,560,354 | B1 | * | 5/2003 | Maurer et al. | ................ 382/131 |
| 2003/0208122 | A1 | * | 11/2003 | Melkent et al. | ............. 600/426 |
| 2005/0096589 | A1 | * | 5/2005 | Shachar | .................... 604/95.01 |
| 2005/0203386 | A1 | * | 9/2005 | Heigl et al. | .................... 600/427 |
| 2005/0281385 | A1 | * | 12/2005 | Johnson et al. | ............. 378/163 |
| 2006/0058616 | A1 | * | 3/2006 | Marquart et al. | ............. 600/407 |

* cited by examiner

*Primary Examiner* — Joel F Brutus
(74) *Attorney, Agent, or Firm* — McAndrews, Held & Malloy, Ltd.; William Baxter

(57) ABSTRACT

Certain embodiments of the present invention provide for a system and method for assessing the accuracy of a surgical navigation system. The method may include acquiring an X-ray image that captures a surgical instrument. The method may also include segmenting the surgical instrument in the X-ray image. In an embodiment, the segmenting may be performed using edge detection or pattern recognition. The distance between the predicted location of the surgical instrument tip and the actual location of the surgical instrument tip may be computed. The distance between the predicted location of the surgical instrument tip and the actual location of the surgical instrument tip may be compared with a threshold value. If the distance between the predicted location of the surgical instrument tip and the actual location of the surgical instrument tip is greater than the threshold value, the user may be alerted.

20 Claims, 7 Drawing Sheets

Surgical Instrument 320

Surgical Instrument Shadow 420

Segmented Instrument Shadow

SYSTEM AND METHOD FOR ACCURACY VERIFICATION FOR IMAGE BASED SURGICAL NAVIGATION

BACKGROUND OF THE INVENTION

The present invention generally relates to a system and method for improving the navigation accuracy of an electromagnetic navigation system for use with medical applications. Particularly, the present invention relates to a system and method for verifying the accuracy of a surgical navigation system.

Electromagnetic type navigation systems are useful in numerous applications. One application of particular use is in medical applications, and more specifically, image guided surgery. Typical image guided surgical systems acquire a set of images of an operative region of a patient's body and track a surgical tool or instrument in relation to one or more sets of coordinates. At the present time, such systems have been developed or proposed for a number of surgical procedures such as brain surgery and arthroscopic procedures on the knee, wrist, shoulder or spine, as well as certain types of angiography, cardiac or other interventional radiological procedures and biopsies. Such procedures may also involve preoperative or intra-operative x-ray images being taken to correct the position or otherwise navigate a tool or instrument involved in the procedure in relation to anatomical features of interest. For example, such tracking may be useful for the placement of an elongated probe, radiation needle, fastener or other article in tissue or bone that is internal or is otherwise positioned so that it is difficult to view directly.

An electromagnetic tracking system may be used in conjunction with an x-ray system. For example, an electromagnetic tracking system may be used in conjunction with a C-arm fluoroscope. The C-arm fluoroscope may utilize an x-ray source at one end of the C-arm and an x-ray detector, or camera, at the other end of the C-arm. The patient may be placed between the x-ray source and the x-ray detector. X-rays may pass from the x-ray source, through the patient, to the x-ray detector where an image is captured. The electromagnetic tracking system may generate an electromagnetic field between the ends of the C-arm so tracking may continue during a surgical procedure.

Currently, an operating surgeon can assess the accuracy of the surgical navigation system in a subjective manner. A surgeon may visually compare the "predicted location" of the navigation instrument with the "actual location" of the same instrument on the intra-operative navigated images acquired during surgery. In current fluoroscopic navigation systems, this process may be referred to as "confirmation shots."

For example, a surgeon may track the "predicted location" of the surgical instrument being used on the navigated fluoroscope image. The surgeon may set up the surgical instrument trajectory defining the surgical planning for the procedure being performed. By leaving the surgical instrument in the planned trajectory in the field of view of the C-arm, the navigation system may display the predicted location of the surgical instrument on the navigated fluoroscope image. The surgeon may then acquire an X-ray image, also called a confirmation shot, and captures it to the navigation screen. The predicted location of the surgical instrument and its actual location, materialized by its radiographic shadow on the navigated image, are visible on the navigated image. The predicted location of the surgical instrument is then superimposed on the navigated image.

By comparing the predicted location of the surgical instrument superimposed on the navigated image with the actual location, which may be shown as a shadow of the surgical instrument, the surgeon may assess the overall system accuracy. If the predicted location matches the actual location on the navigated image, the surgeon may determine the navigation system is accurate. If there is a visible difference between the predicted and actual instrument locations, the surgeon can conclude that the system error is high such that it makes the surgical navigation inaccurate and as a consequence, unsuitable for being used.

One disadvantage to the technique described above is that it provides a subjective method from which the surgeon makes a judgment on whether the navigation system is accurate enough to use. Using this technique to determine whether a navigation system is sufficiently accurate may vary from surgeon to surgeon. Also, a user relying on the navigation system knowing it has some degree of inaccuracy may not have confidence in the navigation system. This may compromise the effectiveness of the navigation system during the surgery.

Accordingly, a system and method is needed to better assess the accuracy of an instrument navigation system. Such a system and method may automate the verification procedure for assessing accuracy of the instrument navigation system.

SUMMARY OF THE INVENTION

Certain embodiments of the present invention may include a method for assessing the accuracy of a surgical navigation system. The method may include acquiring an X-ray image that captures a surgical instrument. The method may also include segmenting the surgical instrument in the X-ray image. In an embodiment, the segmenting the surgical instrument in the X-ray image may be performed using edge detection or pattern recognition. The method may also include computing the distance between the predicted location of the surgical instrument tip and the actual location of the surgical instrument tip. The distance between the predicted location of the surgical instrument tip and the actual location of the surgical instrument tip may be compared with a threshold value. If the distance between the predicted location of the surgical instrument tip and the actual location of the surgical instrument tip is greater than a threshold value, a user may be alerted. The computation of the distance between the predicted location of the surgical instrument tip and the actual location of the surgical instrument tip may be the navigation error in a 3D navigation volume. The navigation error in a 3D navigation volume may be computed by computing a back-projection line that stems from the pixel coordinates of the actual location of the surgical instrument tip and computing the distance between the back-projection line and the 3D coordinates of the predicted location of the surgical instrument tip. The computation of the distance between the predicted location of the surgical instrument tip and the actual location of the surgical instrument tip is the navigation error in a 2D image. The navigation error in a 2D image may be computed by projecting 3D coordinates of the predicted location of the surgical instrument tip onto an image and computing the distance between the predicted projection and the actual projection of the surgical instrument tip on the image.

Certain embodiments of the present invention may include a system for assessing the accuracy of a surgical navigation system. The system may include an x-ray unit for acquiring an X-ray image that captures a surgical instrument. The system may also include a computer unit comprising computer software that segments the surgical instrument in the X-ray image and that computes the distance between the predicted location of the surgical instrument tip and the actual location of the surgical instrument tip. The computer unit may further comprise computer software for comparing the distance between the predicted location of the surgical instrument tip and the actual location of the surgical instrument tip with a threshold value. The computer unit may further comprise computer software for alerting a user if the distance between the predicted location of the surgical instrument tip and the actual location of the surgical instrument tip is greater than the threshold value.

Certain embodiments of the present invention may include a computer readable medium having a set of instructions for execution by a computer. The set of instructions may include an acquisition routine for acquiring an X-ray image that captures a surgical instrument. The set of instructions may also include a segmentation routine for segmenting the surgical instrument in the X-ray image. In an embodiment, the segmentation routine may include edge detection. The set of instructions may also include a computation routine for computing the distance between the predicted location of the surgical instrument tip and the actual location of the surgical instrument tip. The set of instructions may also include a comparison routine for comparing the distance between the predicted location of the surgical instrument tip and the actual location of the surgical instrument tip with a threshold value. The set of instructions may also include an alerting routine for alerting a user if the distance between the predicted location of the surgical instrument tip and the actual location of the surgical instrument tip is greater than the threshold value. The computation routine for computing the distance between the predicted location of the surgical instrument tip and the actual location of the surgical instrument tip may be the navigation error in a 3D navigation volume. The set of instructions may include a set of instructions for computing the navigation error in a 3D navigation volume. The set of instructions for computing the navigation error in a 3D navigation volume may include a first computation routine for computing a back-projection line that stems from the pixel coordinates of the actual location of the surgical instrument tip and a second computation routine for computing the distance between the back-projection line and the 3D coordinates of the predicted location of the surgical instrument tip. The computation routine for computing the distance between the predicted location of the surgical instrument tip and the actual location of the surgical instrument tip may be the navigation error in a 2D image. The set of instructions for computing the navigation error in a 2D image may include a first computation routine for projecting 3D coordinates of the predicted location of the surgical instrument tip onto an image and a second computation routine for computing the distance between the predicted projection and the actual projection of the surgical instrument tip on the image.

Figure 1:
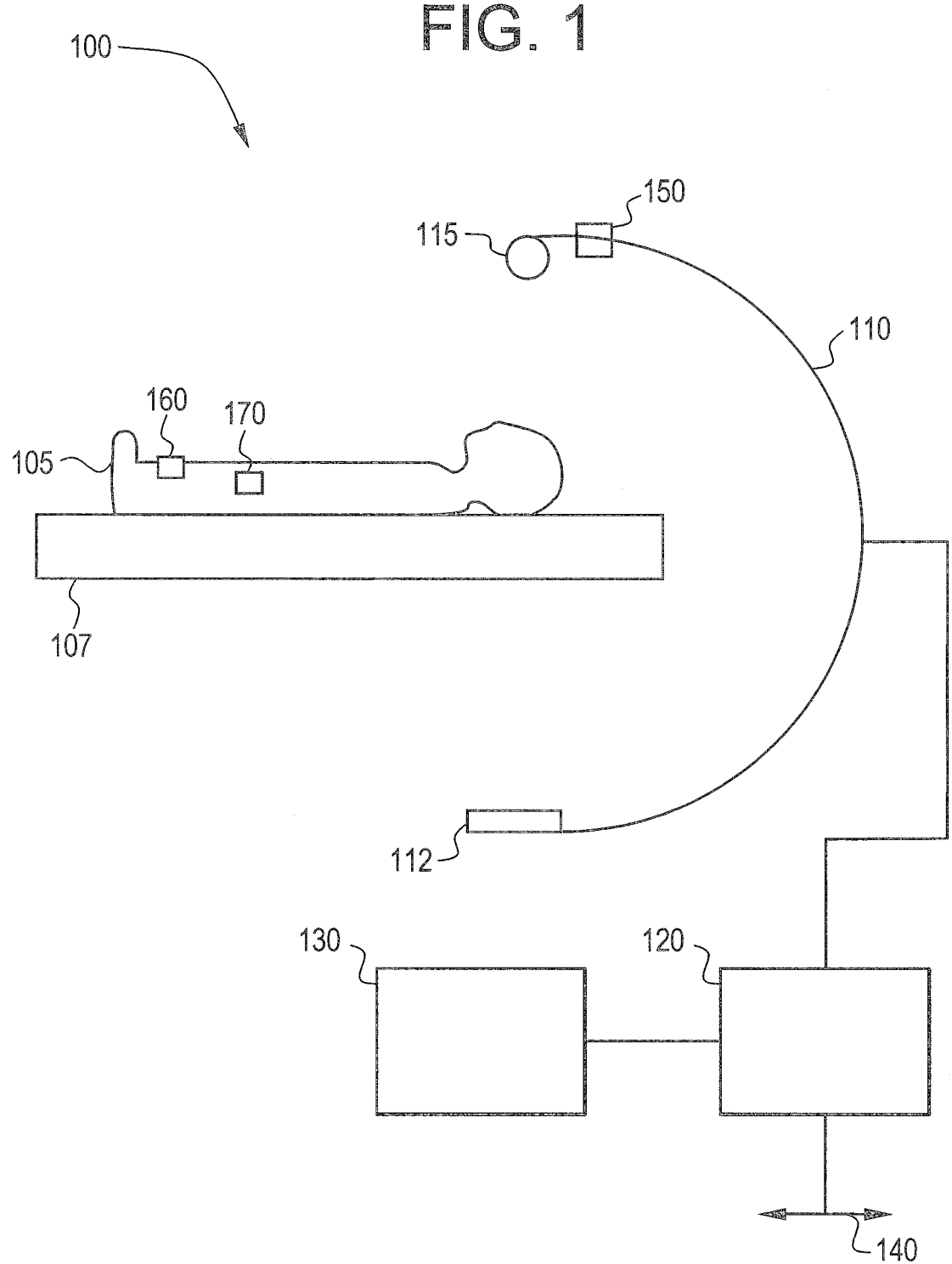
FIG. 1 illustrates a system that may be used for image guided surgery in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 that may be used for image guided surgery in accordance with an embodiment of the present invention. The system 100 illustrates, as an example of a medical imaging unit, a C-arm unit 110. The medical imaging unit, however, may be other medical imaging equipment, such as an ultrasound unit, for example. Accordingly, any medical imaging equipment may be used.

The C-arm unit 110 is connected to a computer unit 120. The connection between the C-arm unit 110 and the computer unit 120 may be wired or wireless. The computer unit 120 may be any equipment or software that permits electronic medical images, such as x-rays, ultrasound, CT, MRI, EBT, MR, or nuclear medicine for example, to be electronically acquired, stored, or transmitted for viewing and operation. The computer unit 120 may receive input from a user. The computer unit 120 represents, in general, equipment and software. The actual physical computer units may be separate units, part of a single unit, a computer system, or part of a computer system.

The computer unit 120 may be connected to other devices via an electronic network. The connection of the computer unit 120 to an electronic network is illustrated by line 140. The connection between the network 140 and the computer unit 120 may be wired or wireless. The computer unit 120 may also be connected to a display unit 130. The connection between the computer unit 120 and the display unit 130 may be wired or wireless. The display unit 130 may be a single display unit or multiple display units. Additionally, the display unit 130 may be a two-dimensional display unit or a three-dimensional display unit, for example. Accordingly, any display unit may be used in accordance with the present invention.

Element 105 represents a patient and element 107 represents a table on which the patient is lying. Elements 150, 160, and 170 are electronic sensors that may identify their location with reference to a reference frame and with reference to each other. Although three sensors 150-170 are shown, any number of sensors may be used. The sensors 150-170 are generally in electronic communication with the computer unit 120. Element 112 represents an x-ray source and element 115 represents an x-ray detector. The x-ray detector 115 may be, for example, an image intensifier or flat panel detector. The electronic communication may be over a wire or may be transmitted in a wireless fashion. The components of the system 100 may be single units, separate units, may be integrated in various forms, and may be implemented in hardware and/or in software.

Figure 2:
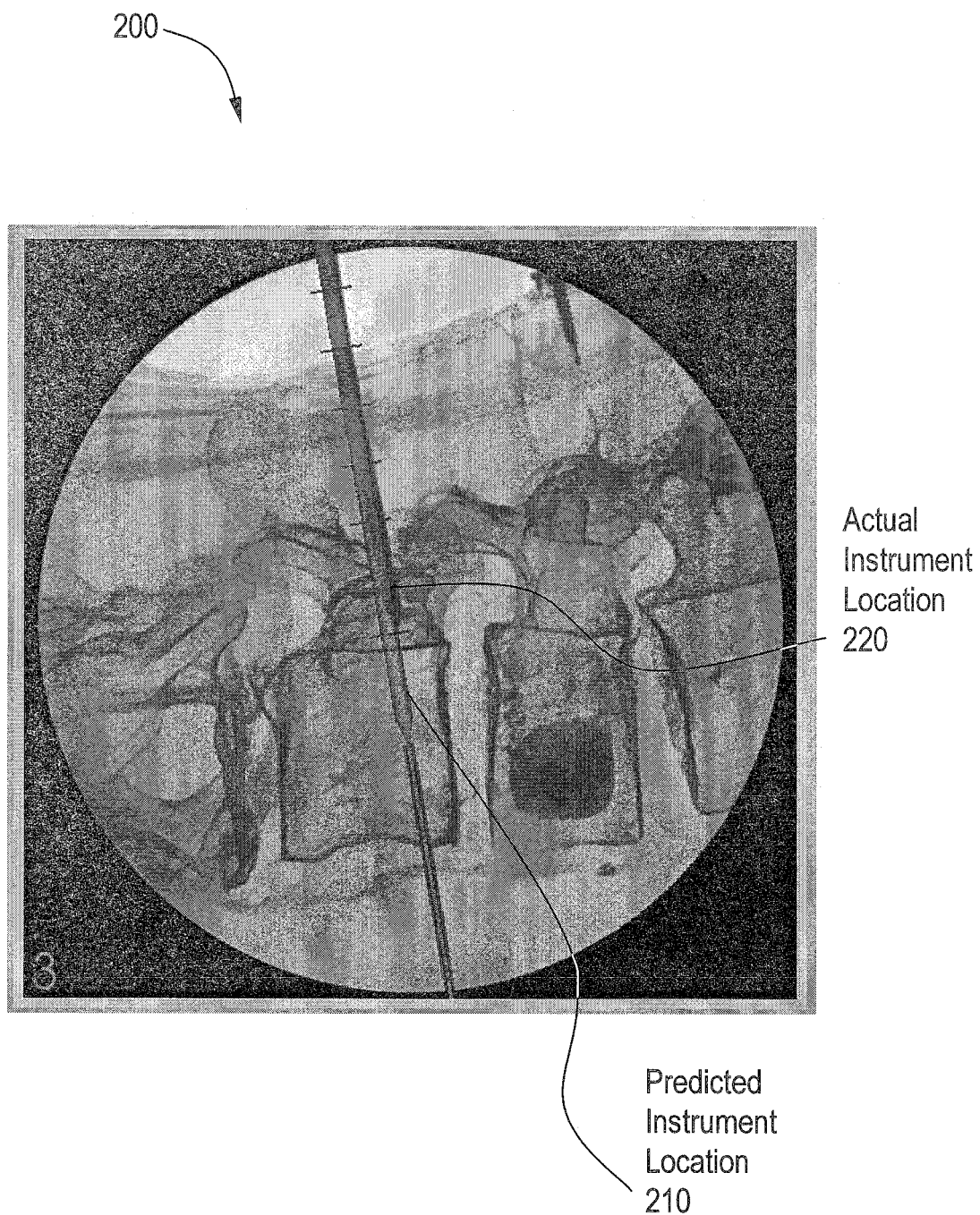
FIG. 2 illustrates a graphic illustrating the predicted instrument location and the actual instrument location.

FIG. 2 illustrates a graphic 200 illustrating the predicted instrument location and the actual instrument location. The graphic 200 illustrates a "confirmation shot" that shows the predicted instrument location 210 superimposed onto the actual instrument location 220 as part of an X-ray of a patient's anatomy. In the embodiment as shown on the graphic 200, the actual instrument location 220 may be illustrated as a shadow on the graphic 200. The graphic 200 is only an example and the actual instrument location 220 and the predicted instrument location 210 may be represented in a manner different than that shown in the graphic 200.

Figure 3:
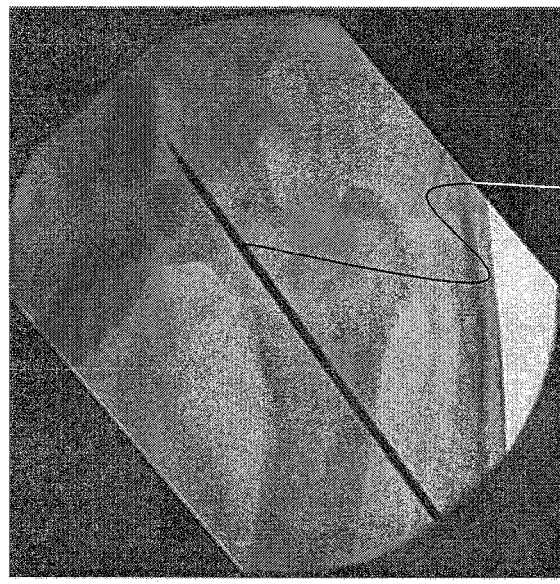
FIG. 3 illustrates an image illustrating the contrast between patient anatomy and a surgical instrument.

FIG. 3 illustrates an image 300 illustrating the contrast between patient anatomy and a surgical instrument. The image 300 illustrates an X-ray image showing the surgical instrument 320. The surgical instrument 320 represents the actual location of the surgical instrument. In an embodiment, the image 300 may represent a "confirmation shot" prior to superposition of the predicted instrument location.

In an embodiment, the image 300 may be segmented by computer software to identify the surgical instrument 320. In an embodiment, computer software may segment and extract the tip of the surgical instrument 320 from the image 300. The segmentation of the surgical instrument 320 may be performed by edge detection or pattern recognition algorithms to achieve an accurate localization of the tip of the surgical instrument 320 within the image 300. The computer software may utilize the contrast between the anatomical structure of the image 300 and the surgical instrument 320.

Figure 4:
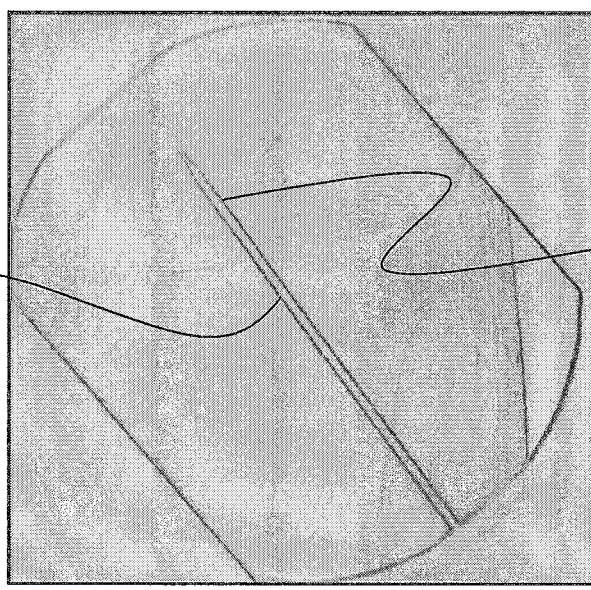
FIG. 4 illustrates an image after edge detection segmentation has been performed.

FIG. 4 illustrates an image 400 which is the image 300 after edge detection segmentation has been performed. The image 400 shows the surgical instrument shadow 420. FIG. 4 is only an example and other type of segmentation may be performed to obtain the surgical instrument shadow.

Once the computer software has located the actual location of the tip of the surgical instrument 320 as illustrated, for example in FIG. 4, the computer software may compute the navigation error between the actual location of the surgical instrument and the predicted location of the surgical instrument. In an embodiment, in order to evaluate the navigation error, two quantities may be computed, the 3D error computation in navigation volume and the 2D error computation in the navigated image.

Figure 5:
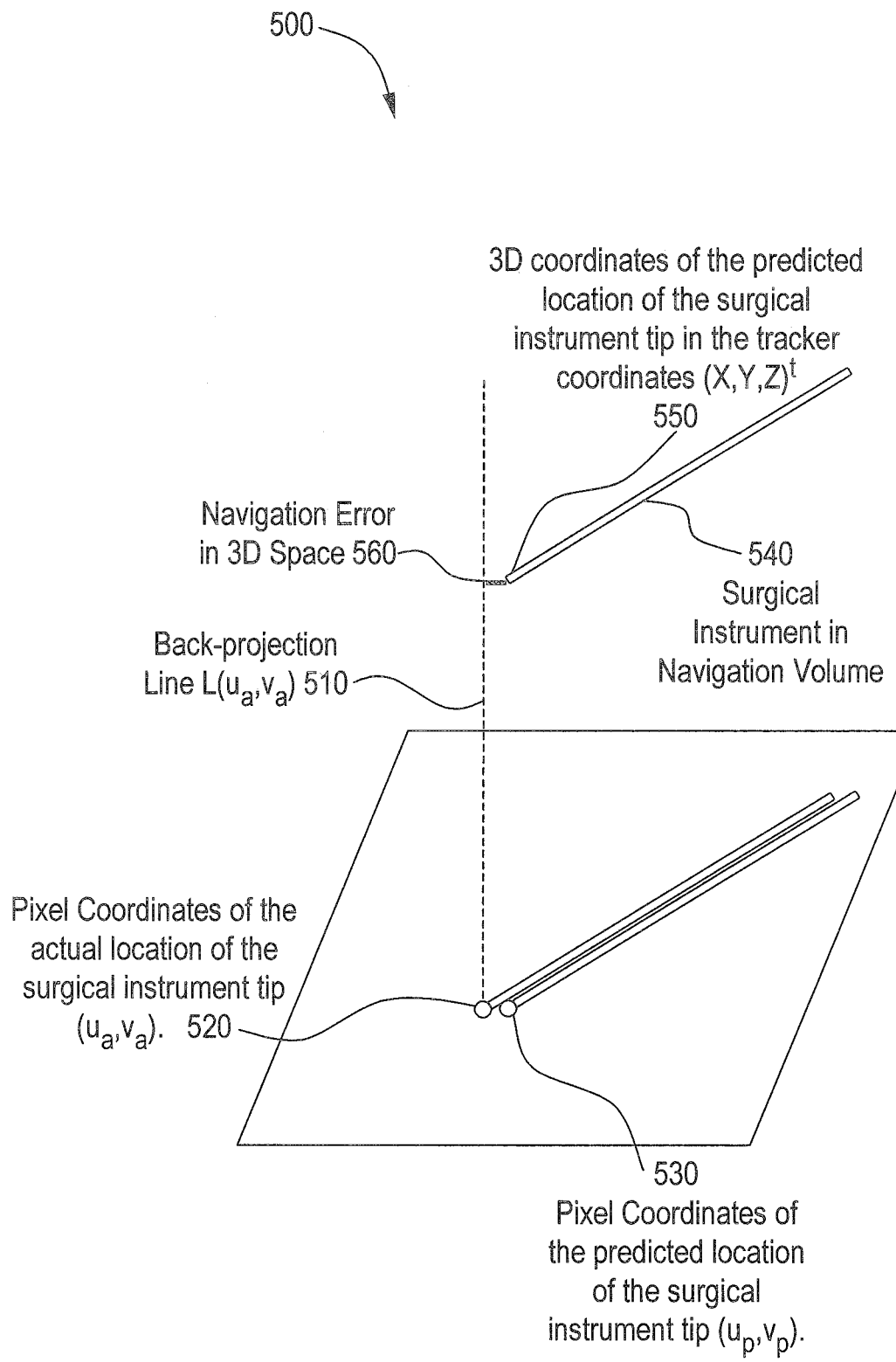
FIG. 5 illustrates a graphic showing the computation of the 3D error in navigation volume.

FIG. 5 illustrates a graphic 500 showing the computation of the 3D error in navigation volume. As shown in the graphic 500, the coordinates 520 $(u_a, v_a)$ denote the pixel coordinates 520 of the actual location of the surgical instrument tip computed using image segmentation in the image. The coordinates 530 $(u_p, v_p)$ denote the pixel coordinates 530 of the predicted location of the surgical instrument tip in the image. The back-projection line 510 $L(u_a, v_a)$ stemming from the pixel coordinates 520 of the actual location of the surgical instrument tip 520 in the image is computed using camera calibration parameters. In an embodiment, the computation of the back-projection line stemming from an image pixel (u,v) is performed once the camera calibration parameters have been computed. The camera calibration is a process that aims at estimating the X-ray image formation model. The estimation enables the system to compute the 2D projection of a 3D point or inversely to compute the back-projection line associated with a 2D pixel within the calibrated image. The output of the camera calibration process is generally referred to as camera parameters or projection parameters. The parameters enable the passage from a 3D point in the space to its 2D projection and the computation, for a 2D pixel, of the back-projection line associated with that pixel. The back-projection line 510 $L(u_a, v_a)$ is computed in the tracker coordinates system.

Also shown in the graphic 500 is the surgical instrument in navigation volume 540. The distance between the back-projection line 510 $L(u_a, v_a)$ and the 3D coordinates of the predicted location of the surgical instrument tip in the tracker coordinates $(X,Y,Z)^t$ 550 is computed. The 3D coordinates of the surgical instrument tip $(X,Y,Z)^t$ 550 in the tracker coordinates system are known because the surgical instrument may be mounted onto an electromagnetic receiver and its tip has previously been calibrated. For example, the surgical instrument tip may be calibrated using fixed points calibration.

The distance between the back-projection line 510 $L(u_a, v_a)$ and the 3D coordinates of the surgical instrument tip $(X,Y,Z)^t$ 550 is the navigation error in the 3D navigation volume 560. The navigation error in 3D navigation volume 560 may be computed as follows:

$$E_{3d} = \text{Distance}[L(u_a, v_a), (X,Y,Z)^t] \qquad \text{Equation 1}$$

where $E_{3d}$ is the navigation error in 3D navigation volume. In Equation 1, the Distance function used to compute the 3D error is the distance between a Line $L(u_a, v_a)$ and a 3D point $(X,Y,Z)^t$. The distance between the Line $L(u_a, v_a)$ and the 3D point $(X,Y,Z)^t$ may be geometrically defined as the length measurement of the line segment stemming from the 3D point and which is perpendicular to the Line $L(u,v)$. This distance is measured in the plane defined by the Line $L(u,v)$ and the 3D point $(X,Y,Z)^t$.

The mathematical formula to compute the distance between the Line $L(u_a, v_a)$ and the 3D point $(X,Y,Z)^t$ may depend on the parameters used to define the 3D line. For example, the distance between the 3D point $(x^0, y^0, z^0)$ and the line L defined as the line that passes through $(x^1, y^1, z^1)$ with its orientation defined by the vector (a,b,c)t is given by:

$$D[L(u_a, v_a)(X, Y, Z)^t] = \sqrt{\frac{\begin{vmatrix} y_0 - y_1 & z_0 - z_1 \\ b & c \end{vmatrix}^2 + \begin{vmatrix} z_0 - z_1 & x_0 - x_1 \\ c & a \end{vmatrix}^2 + \begin{vmatrix} x_0 - x_1 & y_0 - y_1 \\ a & b \end{vmatrix}^2}{a^2 + b^2 + c^2}} \qquad \text{Equation 2}$$

Figure 6:
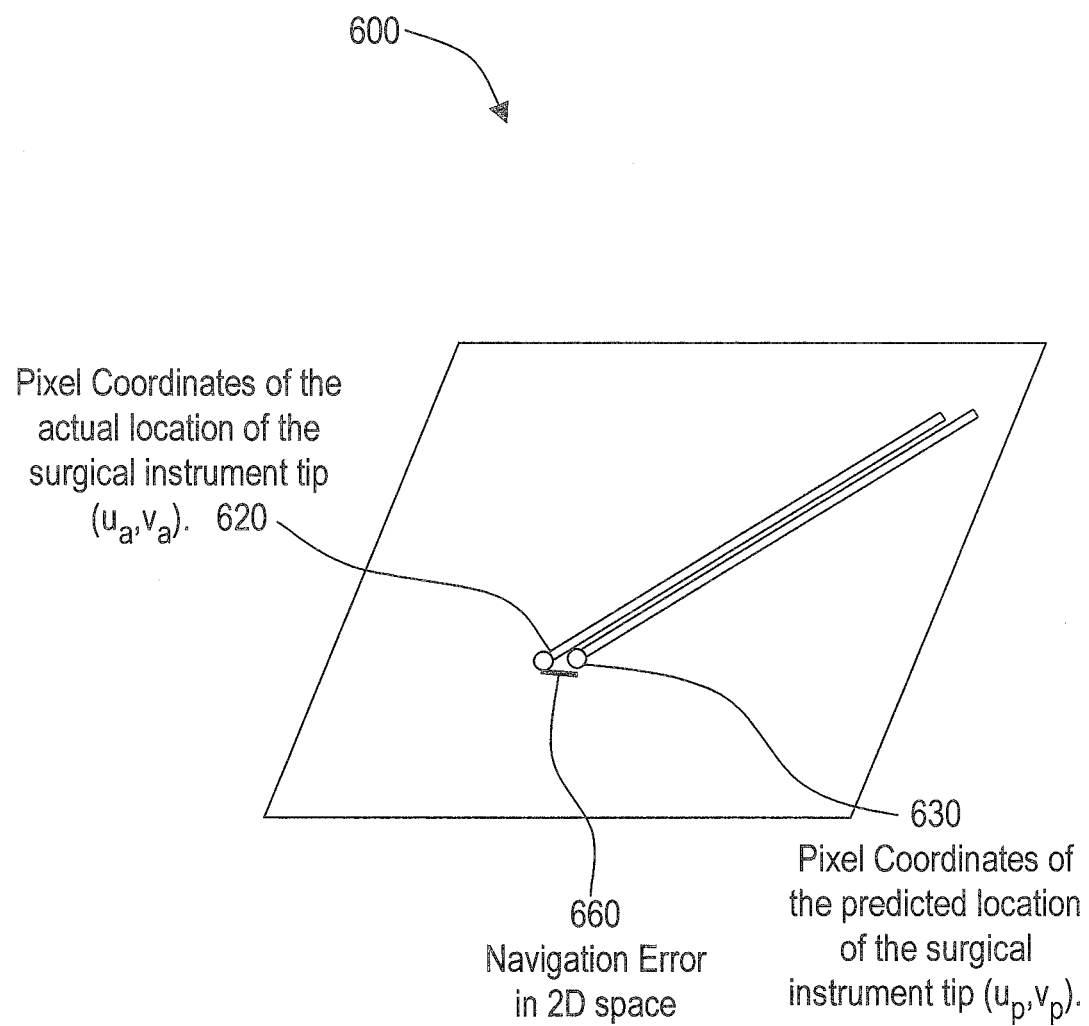
FIG. 6 illustrates a graphic showing the computation of the 2D error in an image.

FIG. 6 illustrates a graphic 600 showing the computation of the 2D error in an image. The 2D error in the image may also be called the 2D projection error. As shown in the graphic 600, the 3D coordinates of the predicted location of the surgical instrument tip $(X,Y,Z)^t$ are projected onto the image using camera projection parameters and performing a projection operation. In an embodiment, the computation of the back-projection line stemming from an image pixel (u,v) is performed once the camera calibration parameters have been computed. The camera calibration is a process that aims at estimating the X-ray image formation model. The estimation enables the system to compute the 2D projection of a 3D point or inversely to compute the back-projection line associated with a 2D pixel within the calibrated image. The output of the camera calibration process is generally referred to as camera parameters or projection parameters.

The parameters enable the passage from a 3D point in the space to its 2D projection and the computation, for a 2D pixel, of the back-projection line associated with that pixel. The projection of the 3D coordinates of the predicted location of the surgical instrument yields the predicted 2D instrument location on the image. The coordinates 630 ($u_p, v_p$) denote the pixel coordinates 630 of the predicted location of the surgical instrument tip in the image. The coordinates 620 ($u_a, v_a$) denote the pixel coordinates 620 of the actual location of the surgical instrument tip computed using image segmentation in the image.

The distance between the predicted projection 630 ($u_p, v_p$) and the actual projection 620 ($u_a, v_a$) of the surgical instrument tip on the image is the 2D navigation error 660 in the image. The 2D navigation error 660 in the image may also be called the 2D navigation error in the confirmation shot. The 2D navigation error 660 may be computed as follows:

$$E_{2d} = D = sqrt[(u_p - u_a)^2 + (v_p - v_a)^2]$$ Equation 3

The distance D is the difference in 2D image space between the predicted location of the surgical instrument tip 630 and the actual location of the surgical instrument tip 620. The distance D is equal to the 2D navigation error 660, $E_{2d}$.

Accordingly, the navigation error in 3D navigation volume 560 and the 2D navigation error 660 may be computed and quantified. In accordance with an embodiment of the present invention, the quantified error values may be compared with a threshold error value. In an embodiment, if one of the quantified error values is greater than the associated threshold error value, the user may be alerted that the navigation system is inaccurate. It should be noted that it is not necessary that both the navigation error in 3D navigation volume 560 and the 2D navigation error 660 are used. In an embodiment one of the values may be used. In another embodiment, both of the values may be used. The embodiments of the present invention free the surgeon from determining whether the surgical navigation system is accurate.

Figure 7:
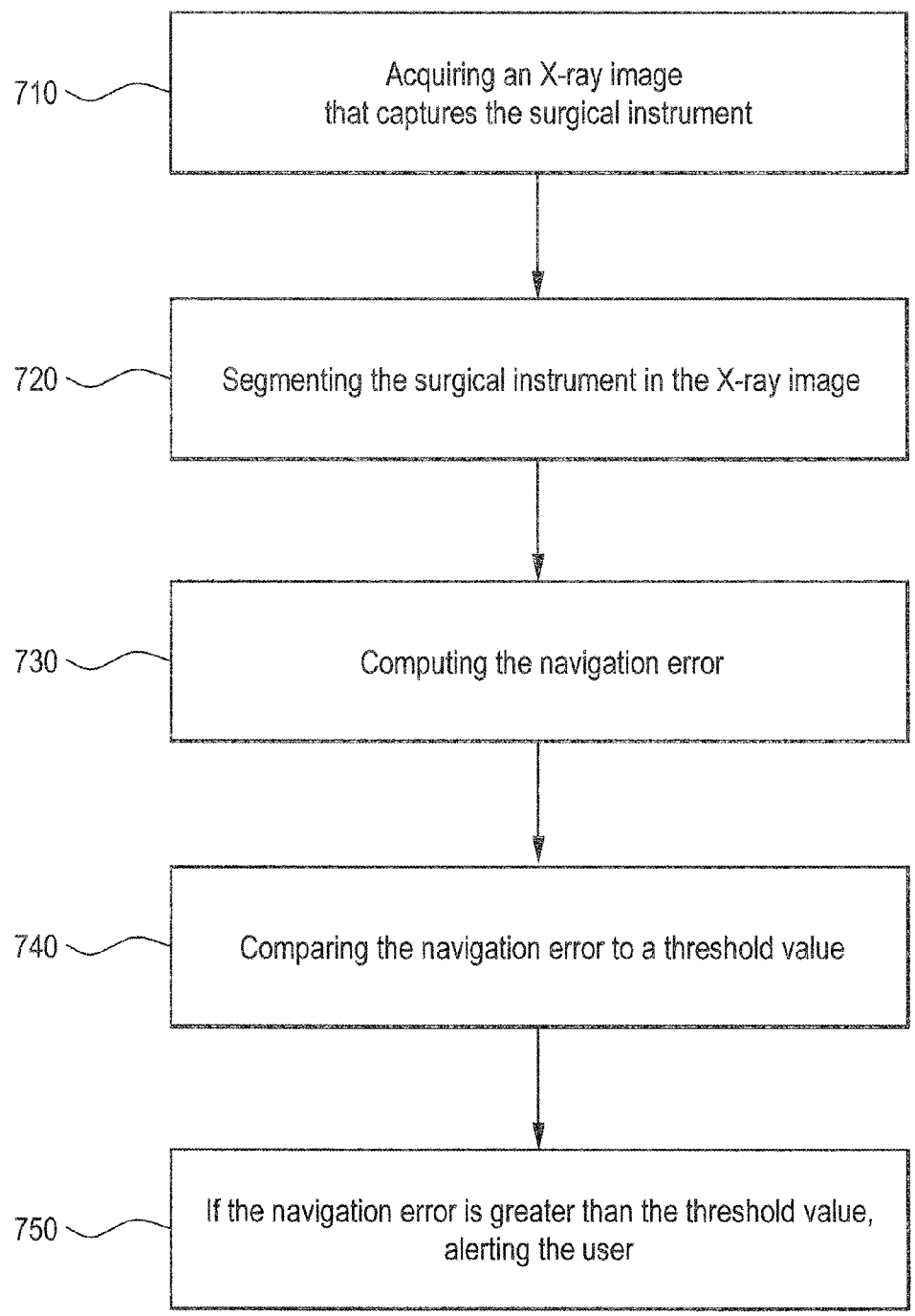
FIG. 7 illustrates a method for assessing the accuracy of a surgical navigation system in accordance with an embodiment of the present invention.

FIG. 7 illustrates a method 700 for assessing the accuracy of a surgical navigation system in accordance with an embodiment of the present invention. At step 710, an X-ray image that captures the surgical instrument is acquired. In an embodiment, the X-ray image may be a confirmation shot. At step 720, the X-ray image acquired at step 710 may be segmented. The segmenting may include image processing in order to segment and extract the tip of the surgical instrument in the X-ray image. In an embodiment, the segmentation of the surgical instrument may be performed using an edge detection or pattern recognition algorithm to achieve accurate localization of the surgical instrument tip within the X-ray image. At step 730, the navigation error between the predicted location of the surgical instrument tip and the actual location of the surgical instrument tip is computed. In an embodiment, the navigation error may be the navigation error in a 3D navigation volume. In an embodiment the navigation error may be the 2D navigation error. At step 740, the navigation error may be compared to a threshold value. If the navigation error is greater than a threshold value, at step 750 a user may be alerted that the surgical navigation system is operating with insufficient accuracy.

Figure 8:
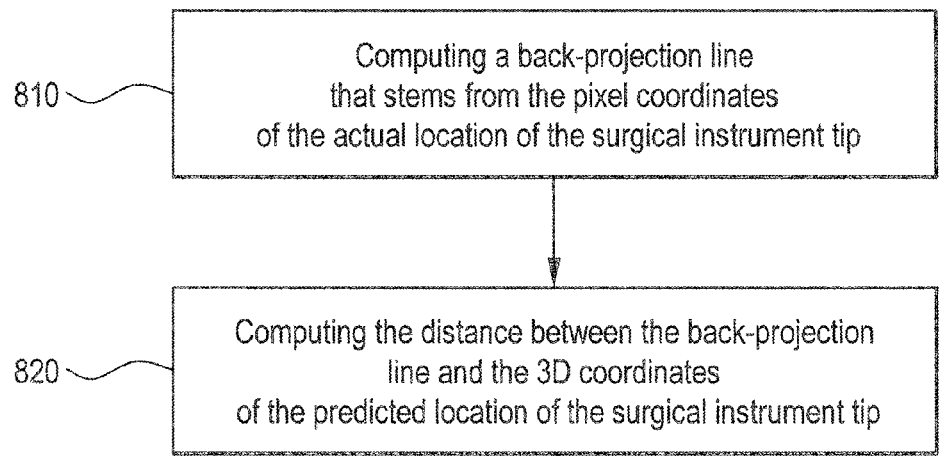
FIG. 8 illustrates a method for computing the navigation error in a 3D navigation volume.

FIG. 8 illustrates a method 800 for computing the navigation error in a 3D navigation volume. At step 810, a back-projection line that stems from the pixel coordinates of the actual location of the surgical instrument tip is computed. The back-projection line is computed in the tracker coordinates system. In an embodiment, the computation of the back-projection line stemming from an image pixel (u,v) is performed once the camera calibration parameters have been computed. The camera calibration is a process that aims at estimating the X-ray image formation model. The estimation enables the computation of the 2D projection of a 3D point or inversely to compute the back-projection line associated with a 2D pixel within the calibrated image. The output of the camera calibration process is generally referred to as camera parameters or projection parameters. The parameters enable the passage from a 3D point in the space to its 2D projection and the computation, for a 2D pixel, of the back-projection line associated with that pixel.

At step 820, the distance between the back-projection line and the 3D coordinates of the predicted location of the surgical instrument tip is computed. The 3D coordinates of the surgical instrument tip in the tracker coordinates system are known because the surgical instrument may be mounted onto an electromagnetic receiver and its tip has previously been calibrated. For example, the surgical instrument tip may be calibrated using fixed points calibration. In an embodiment, the distance between the back-projection line and the 3D coordinates of the surgical instrument tip is the navigation error in the 3D navigation volume.

Figure 9:
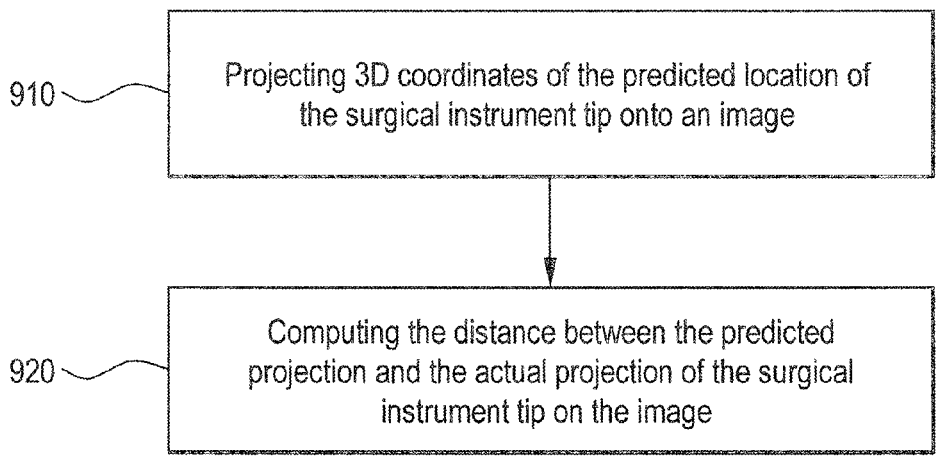
FIG. 9 illustrates a method for computing the navigation error in a 2D image.

FIG. 9 illustrates a method 900 for computing the navigation error in a 2D image. At step 910, 3D coordinates of the predicted location of the surgical instrument tip are projected onto an image. In an embodiment, the 3D coordinates of the predicted location of the surgical instrument tip are projected onto the image using camera projection parameters. The projection of the 3D coordinates of the predicted location of the surgical instrument yields the predicted 2D instrument location on the image.

At step 920, the distance between the predicted projection and the actual projection of the surgical instrument tip on the image is computed. In an embodiment, the distance between the predicted projection and the actual projection of the surgical instrument tip on the image is the 2D navigation error in the image. The 2D navigation error in the image may also be called the 2D navigation error in the confirmation shot.

The system and method 700 described above may be carried out as part of a computer-readable storage medium including a set of instructions for a computer. The set of instructions may include an acquisition routine for acquiring an X-ray image that captures the surgical instrument. In an embodiment, the X-ray image may be a confirmation shot. The set of instructions may also include a segmentation routine for segmenting the acquired X-ray image. The segmenting may include image processing in order to segment and extract the tip of the surgical instrument in the X-ray image. In an embodiment, the segmentation of the surgical instrument may be performed using an edge detection or pattern recognition algorithm to achieve accurate localization of the surgical instrument tip within the X-ray image. The set of instructions may also include a computation routine for computing the navigation error between the predicted location of the surgical instrument tip and the actual location of the surgical instrument tip. In an embodiment, the navigation error may be the navigation error in a 3D navigation volume. In an embodiment the navigation error may be the 2D navigation error. The set of instructions may also include a comparison routine for comparing the navigation error with a threshold value. The set of instructions may also include an alerting routine for alerting a user if the navigation error is greater than a threshold value that the surgical navigation system may be operating with insufficient accuracy.

The system and method 800 described above may be carried out as part of a computer-readable storage medium including a set of instructions for a computer. The set of instructions may include a first computation routine for computing a back-projection line that stems from the pixel coordinates of the actual location of the surgical instrument tip. In an embodiment, the back-projection line is computed in the tracker coordinates system. The set of instructions may also include a second computation routine for computing the distance between the back-projection line and the 3D coordinates of the predicted location of the surgical instrument tip. The 3D coordinates of the surgical instrument tip in the tracker coordinates system are known because the surgical instrument may be mounted onto an electromagnetic receiver and its tip has previously been calibrated. For example, the surgical instrument tip may be calibrated using fixed points calibration. In an embodiment, the distance between the back-projection line and the 3D coordinates of the surgical instrument tip is the navigation error in the 3D navigation volume.

The system and method 900 described above may be carried out as part of a computer-readable storage medium including a set of instructions for a computer. The set of instructions may include a first computation routine for projecting the 3D coordinates of the predicted location of the surgical instrument tip onto an image. In an embodiment, the 3D coordinates of the predicted location of the surgical instrument tip are projected onto the image using camera projection parameters. The projection of the 3D coordinates of the predicted location of the surgical instrument yields the predicted 2D instrument location on the image. The set of instructions may also include a second computation routine for computing the distance between the predicted projection and the actual projection of the surgical instrument tip on the image. In an embodiment, the distance between the predicted projection and the actual projection of the surgical instrument tip on the image is the 2D navigation error in the image. The 2D navigation error in the image may also be called the 2D navigation error in the confirmation shot.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for assessing an accuracy of a surgical navigation system, the method comprising:
   acquiring an X-ray image capturing a surgical instrument tip;
   tracking a tracked location of the surgical instrument tip;
   segmenting the surgical instrument tip in the X-ray image to determine an imaged location of the surgical instrument tip; and
   computing a distance between the tracked location of the surgical instrument tip and the imaged location of the surgical instrument tip to form a navigation error of the surgical navigation system.

2. The method of claim 1, comprising comparing the distance between the tracked location of the surgical instrument tip and the imaged location of the surgical instrument tip with a threshold value.

3. The method of claim 2, comprising alerting a user if the navigation error of the surgical navigation system is greater than the threshold value.

4. The method of claim 1, wherein the computing the distance between the tracked location of the surgical instrument tip and the imaged location of the surgical instrument tip comprises:
   computing a back-projection line stemming from the imaged location of the surgical instrument tip; and
   computing a distance between the back-projection line and the tracked location of the surgical instrument tip.

5. The method of claim 1, wherein the computing the distance between the tracked location of the surgical instrument and the imaged location of the surgical instrument tip comprises:
   projecting 3D coordinates of the tracked location of the surgical instrument tip onto an image to form a tracked projection; and
   computing a distance between the tracked projection of the surgical instrument tip and an imaged projection of the surgical instrument tip on the image.

6. The method of claim 1, wherein the tracking the tracked location of the surgical instrument tip comprises tracking the tracked location of the surgical instrument tip with an electromagnetic tracking system.

7. The method of claim 1, wherein the tracking the tracked location of the surgical instrument tip comprises tracking the tracked location of the surgical instrument tip according to a planned trajectory of the surgical instrument tip.

8. A system for assessing an accuracy of a surgical navigation system, the system comprising:
   an X-ray unit configured to acquire an X-ray image capturing a surgical instrument tip;
   a tracking system configured to track a tracked location of the surgical instrument tip; and
   a computer unit configured to segment the surgical instrument tip in the X-ray image to form an imaged location of the surgical instrument tip, the computer unit configured to compute the distance between the tracked location of the surgical instrument tip and the imaged location of the surgical instrument tip to form a navigation error of the surgical navigation system.

9. The system of claim 8, wherein the computer unit is configured to compare the navigation error of the surgical navigation system with a threshold value.

10. The system of claim 9, wherein the computer unit is configured to alert a user if the navigation error of the surgical navigation system is greater than the threshold value.

11. The system of claim 8, wherein the tracking system comprises an electromagnetic tracking system.

12. The system of claim 8, wherein the tracking system is configured to track the tracked location of the surgical instrument tip according to a planned trajectory of the surgical instrument tip.

13. A non-transitory computer readable medium having a set of instructions for execution by a computer, the set of instructions comprising:
   an acquisition routine for acquiring an X-ray image capturing a surgical instrument tip;
   a segmentation routine for segmenting the surgical instrument tip in the X-ray image to determine an imaged location of the surgical instrument tip; and
   a computation routine for computing the distance between a tracked location of the surgical instrument tip from a tracking system and the imaged location of the surgical instrument tip to form a navigation error of the surgical navigation system.

14. The set of instructions of claim 13, comprising a comparison routine to compare the navigation error of the surgical navigation system with a threshold value.

15. The set of instructions of claim 14, comprising an alerting routine to alert a user if the navigation error of the surgical navigation system is greater than the threshold value.

16. The set of instructions of claim 13, wherein the computation routine computes the navigation error of the surgical navigation system in a 3D navigation volume.

17. The set of instructions of claim 16, comprising:
a first computation routine for computing a back-projection line stemming from pixel coordinates of the imaged location of the surgical instrument tip; and
a second computation routine for computing a distance between the back-projection line and pixel coordinates of the tracked location of the surgical instrument tip.

18. The set of instructions of claim 13, comprising:
a first computation routine for projecting 3D coordinates of the tracked location of the surgical instrument tip onto an image; and,
a second computation routine for computing a distance between the tracked projection and an imaged projection of the surgical instrument tip on the image.

19. The set of instructions of claim 13, wherein the tracking system comprises an electromagnetic tracking system.

20. The set of instructions of claim 13, wherein the tracked location of the surgical instrument tip is tracked according to a planned trajectory of the surgical instrument tip.

* * * * *